United States Patent
Talor

(10) Patent No.: US 6,896,879 B2
(45) Date of Patent: May 24, 2005

(54) METHOD OF PRE-SENSITIZING CANCER PRIOR TO TREATMENT WITH RADIATION AND/OR CHEMOTHERAPY AND A NOVEL CYTOKINE MIXTURE

(75) Inventor: Eyal Talor, Baltimore, MD (US)

(73) Assignee: CEL-SCI Corporation, Vienna, VA (US)

( * ) Notice: Subject to any disclaimer, the term of this patent is extended or adjusted under 35 U.S.C. 154(b) by 61 days.

(21) Appl. No.: 10/611,914

(22) Filed: Jul. 3, 2003

(65) Prior Publication Data

US 2005/0002896 A1 Jan. 6, 2005

(51) Int. Cl.$^7$ .......................... A61K 45/00; A61K 38/21
(52) U.S. Cl. .................... 424/85.1; 424/85.2; 424/85.4; 424/85.5
(58) Field of Search ............................... 424/85.1–85.2, 424/85.4–85.5

(56) References Cited

U.S. PATENT DOCUMENTS

| | | | |
|---|---|---|---|
| 4,401,756 A | 8/1983 | Gillis | |
| 5,632,983 A | 5/1997 | Hadden | |
| 5,698,194 A | 12/1997 | Hadden | |
| 2002/0146397 A1 | 10/2002 | Hadden | |
| 2002/0150541 A1 | 10/2002 | Lau et al. | |
| 2002/0150552 A1 | 10/2002 | Lau et al. | |
| 2003/0124136 A1 | 7/2003 | Hadden | |
| 2003/0129162 A1 | 7/2003 | Lau et al. | |
| 2003/0206885 A1 | 11/2003 | Hadden | |

*Primary Examiner*—Gary B. Nickol
(74) *Attorney, Agent, or Firm*—Sherman & Shalloway

(57) ABSTRACT

This invention relates to a breakthrough method for pre-sensitizing cancer prior to a therapeutic treatment such as chemotherapy, radiation therapy or immuno-therapy and a novel cytokine mixture used in the method thereof. The cytokine mixture is a serum-free and mitogen-free mixture comprised of specific ratios of cytokines such as IL-1$\beta$, TNF-$\alpha$, IFN-$\gamma$ and GM-CSF to Interleukin 2 (IL-2), which is effective in inducing cancerous cells to enter a proliferative cell cycle phase thereby increasing their vulnerability to chemotherapy, radiation therapy and immuno-therapy. One such novel cytokine mixture is Multikine®, which can be used alone or in combination with other drugs for the treatment of cancer thereby increasing the success of cancer treatment and the disease free survival of cancer patients.

4 Claims, 2 Drawing Sheets

METHOD OF PRE-SENSITIZING CANCER PRIOR TO TREATMENT WITH RADIATION AND/OR CHEMOTHERAPY AND A NOVEL CYTOKINE MIXTURE

The patent or application contains at least one drawing executed in color. Copies of this application or patent application publication with color drawings(s) will be provided by the Office upon request and payment of the necessary fee.

INTRODUCTION

This invention relates to a breakthrough method for pre-sensitizing cancer prior to a therapeutic treatment such as chemotherapy, radiation therapy or immuno-therapy and a novel cytokine mixture used in the method thereof. The cytokine mixture is a serum-free and mitogen-free mixture comprised of specific ratios of cytokines such as IL-1β, TNF-α, IFN-γ and GM-CSF to Interleukin 2 (IL-2), which is effective in inducing cancerous cells to enter a proliferative cell cycle phase thereby increasing their vulnerability to chemotherapy, radiation therapy and immuno-therapy. One such novel cytokine mixture is Multikine®, which can be used alone or in combination with other drugs for the treatment of cancer thereby increasing the success of cancer treatment and the disease free survival of cancer patients.

BACKGROUND OF THE INVENTION

Current treatments of cancer and in particular solid tumors, comprise mainly of surgical intervention followed by radiation therapy and/or chemotherapy. Dunne-Daly CF, "Principles of radiotherapy and radiobiology", *Semin Oncol Nurs.* 1999 November;15(4):250–9; Hensley M L et al., "American Society of Clinical Oncology clinical practice guidelines for the use of chemotherapy and radiotherapy protectants. ", *J Clin Oncol.* 1999 October;17(10):3333–55.In conjunction with such therapies, toxic chemotherapeutic agents such as Gemcidabin, Vinblastine, Cisplatin, Fluorouracil, Gleevec, Methotrexate, which are unable to differentiate between normal and cancerous cells, are used. While effective, these and other toxic chemotherapeutic agents have done little to increase overall patient survival. Moreover, current treatments in general also failed to improve 5-year survival rate of cancer patients despite synergistic combination of chemotherapies and radiotherapies. Even anti-epidermal growth factor receptor agents, anti-angiogenic drugs and immuno and immuno-adjuvant therapy using drugs such as Rituximab, Erbitux and Herceptin have failed to significantly increase the 5-year survival rate of cancer patients. Furthermore, complete remission or disease free survival of cancer patient irrespective of cancer type have not been improved upon by any of the aforementioned therapies or synergistic combinations thereof.

One treatment modality investigated to improve disease-free survival rates or lead to complete remission is manipulation of cell-division cycle of cancerous cells. In particular, cycling tumor cells are generally more vulnerable to radio- and chemotherapies than non-cycling tumor cells because complex biochemical and biomolecular processes such as enzyme-dependent DNA replication, enzyme-dependent phosphorylation, signal cascades, association and dissociation of transcriptional activating molecular complexes, and formation and dissociation of macromolecular assemblies of cytostructural elements are required during cell cycling. By inducing tumor cells into a cell cycle phase, anti-metabolic agents that inhibit any of the complex biochemical processes such as ribonucleotide reductase (RNR) inhibitors, dihydrofolate reductase inhibitors or DNA polymerase inhibitors can be used to stop cell cycling and thereby prevent tumor proliferation.

However, known methods taking advantage of cell cycling are limited to synchronizing cell cycle arrest with sequential applications of a chemotherapeutic agent. For example, one known method arrests malignant cells within a S phase of the cell cycle with pyrimidine analogs followed by exposure to high concentrations of anti-metabolites. B. Bhutan et al., Cancer Res. 33:888–894 (1973). Few or no cells in the population can proceed beyond this point of detention after application of the anti-metabolite. W Vogel et al., Hum. Genet. 45:193–8 (1978).

Other efforts include methods of manipulating the cell-division cycle by altering the cell cycle distribution within the cell population. These protocols stimulate malignant cells from a dormant phase into a cell cycling phase thereby increasing their vulnerability to anti-metabolic drugs acting during the vulnerable DNA replication phase. H H Euler et al., Ann. Med. Inteme. (Paris) 145:296–302 (1994); B C Lampkin et al., J. Clin. Invest. 50:2204–14 (1971); Alama et al., Anticancer Res. 10:853–8 (1990). Conversely, other known methods prohibit normal cells from entering S phase thereby protecting normal cells from chemotactic drugs.

Still another known method of synchronizing cell cycle phase with chemotherapeutics is a so-called pulse dose chemotherapy described by R E Moran et al., Cancer Treat. Rep. 64:81–6, (1980). In this approach, leukemic tumor cells in mice were detained in a S phase of the cell cycle with an infusion of hydroxyurea. After the infusion, the cells were "released" to continue cell cycling wherein a "pulse" of a second agent (Ara-C) was given to the mice. The intent was to maximize impact of the second agent as the cycling cells were moving through the vulnerable cell cycle S-phase. However, the results indicated that while mice treated with Ara-C just after the hydroxyurea infusion showed improved survival, mice treated with Ara-C at later times after the hydroxyurea infusion did not show improved survival. Clearly, simply synchronizing cell cycling with a second agent acting non-simultaneously did not improve the action of the two agents.

Nevertheless, known methods taking advantage of cell cycle continue to seek an optimal but passive synergy between dosage, pharmacokinetics, sequence and scheduling.

It might be expected that confining a cell population to a vulnerable cell cycle phase where cells are specifically vulnerable to damage might shift the dynamics of cell killing toward greater efficiency with a greater reduction in side-effects by diminishing exposure to toxic drugs. However, actual experiments taking advantage of cell cycle arrest or static synchronization have been disappointing because known methods are unable to actually induce cells into a cell cycle. Rather, all the known methods simply time the synergistic combination of cell cycle arrest or static synchronization with the target cell population. Moreover, agents such as pyrimidine and hydroxyurea used to effect the cell cycle can cause damage to normal cells.

Another approach would, of course, be to induce the cells to enter into a cell cycle phase as opposed to arresting the cell cycle or synchronizing the cell cycle. However, as would be otherwise predicted from the art, inducing cells into cell cycling increases the risk of a rapidly growing and recurring tumor. But the continued failure of known compositions to improve disease-free survival rates or lead to complete remission suggests a need for inducing malignant cells into cell cycling in a manner that does not proliferate the tumor but increases the susceptibility of the residual tumor to follow-on treatment with radiation and/or chemotherapy.

Therefore, there is a need for methods for inducing tumor cells into a cell cycle selected from the group of (different phases of the cell cycle) $G_1$, S, $G_2$ and M where the new methods can be synergistically applied with chemotherapy, immuno-therapy and radiation therapy. There is also a need for pre-sensitizing cancer tumors in general along with the need for a new serum-free and mitogen-free cytokine mixture comprised of specific ratios of IL-1β to IL-2, TNF-α to IL-2, IFN-γ to IL-2 and GM-CSF to IL-2 that unexpectedly demonstrates far better efficacy over known compositions in inducing a tumor cells to enter a cell cycle phase or for pre-sensitizing a cancer.

SUMMARY OF THE INVENTION

The present invention is based, in part, on methods of pre-sensitizing cancer in general and a new serum-free and mitogen-free cytokine mixture having specific ratios of IL-1β to IL-2, TNF-α to IL-2, IFN-γ to IL-2 and GM-CSF to IL-2. Accordingly, the present invention enables the development of compositions useful as a pharmaceutical or as an adjuvant to be used in conjunction with therapeutic cancer treatments such as chemotherapy, immuno-therapy and radiation therapy.

In embodiments of the invention, a method of improving conventional chemotherapy or radiotherapy of neoplasms or diseases of the immune system with a serum-free and mitogen-free cytokine mixture is disclosed. The methods provide for a pre-sensitizing step for the treatment of cancer in conjunction with radiotherapies or other physical modalities of cell killing. A method for inducing tumor cells into a vulnerable cell cycle phase selected from the group of (different phases of the cell cycle) $G_1$, S, $G_2$ and M is also contemplated. The present invention is not limited to any one particular type of cancer and can include any type of cancer. Specific applications include administering a serum-free and mitogen-free cytokine mixture peritumorally three times a week over a two week period in a range from about 20 IU to 1600 IU or specifically at 400 IU or at 800 IU or still further at five times a week in a range from about 20 IU to 1600 IU or at 400 IU or at 800 IU, wherein IU represent International Units for Interleukin-2 given in World Health Organization $1^{st}$ International Standard for Human IL-2, 86/504.

Another embodiment includes a serum-free and mitogen-free cytokine preparation such as Multikine® in novel and non-obvious concentrations. The cytokine preparation may further be part of a pharmaceutical composition. In specific applications, the new serum-free and mitogen-free cytokine preparation has specific ratios of cytokine to interleukin 2 (IL-2) as follows: IL-1β to IL-2 at a ratio range of 0.4–1.5, and preferably at 0.7+/−0.1 (IL-1β/IL-2), TNF-α to IL-2 at a ratio range of 3.2–10.9, and preferably at 9.5+/−1.8 (TNF-α/IL-2), IFN-γ to IL-2 at a ratio range of 1.5–10.9, and preferably at 6.0+/−1.1 (IFN-γ/IL-2), and GM-CSF to IL-2 at a ratio range of 2.2–4.8, and preferably at 4.0+/−0.5 (GM-CSF/IL-2).

In other specific applications, the serum-free and mitogen-free cytokine preparation or pharmaceutical composition has further different cytokines and other small biologically active molecules in Multikine® wherein the ratio of each of the small biologically active molecules to Il-2 is as follows: IL-3 to Il-2 in a ratio range of 0.38–0.68, preferably at 0.53+/−0.15, IL-6 to Il-2 in a ratio range of 37.2–53.8, preferably at 46+/−5.9, IL-8 to Il-2 in a ratio range of 261–561.5, preferably at 41+/−10.6, IL-1α to Il-2 in a ratio range of 0.56–0.94, preferably at 0.75+/−0.19, IL-1β to Il-2 in a ratio range of 2.87–3.22, preferably at 3.0+/−0.18, IL-16 to Il-2 in a ratio range of 1.24–2.84, preferably at 1.84+/−0.68, G-CSF to Il-2 in a ratio range of 2.16–3.78, preferably at 2.97+/−0.81, TNF-β to Il-2 in a ratio range of 1.18–2.43, preferably at 1.8+/−0.63, MIP-1α to Il-2 in a ratio range of 16.78–37.16, preferably at 22.7+/− 7.0, MIP-1β to Il-2 in a ratio range of 19.2–26.4, preferably at 22.8+/−5.7, a RANTES to Il-2 in a ratio range of 2.3–2.7, preferably at 2.5+/−0.13, a EGF to Il-2 in a ratio range of 0.27–0.28, preferably at 0.275+/−0.008, $PGE_2$ to Il-2 in a ratio range of 3.68–5.42, preferably at 4.5+/−0.87 and $TxB_2$ to Il-2 in a ratio range of 23.5–25.1, preferably at 24.3+/− 0.83.

Other objects and advantages of the present invention are set forth in the following description. The accompanying drawings and tables, which constitute a part of the disclosure, illustrate and, together with the description, explain the principle of the invention. One of ordinary skill in the art will appreciate that other aspects of this invention will become apparent upon reference to the attached figures and the following detailed description.

BREIF DESCRIPTION OF THE DRAWINGS

The invention will now be explained in greater detail by the following description and specific embodiments and with the aid of the accompanying drawings.

DETAILED DESCRIPTION OF THE INVENTION AND PREFERRED EMBODIMENTS

Figure 1:
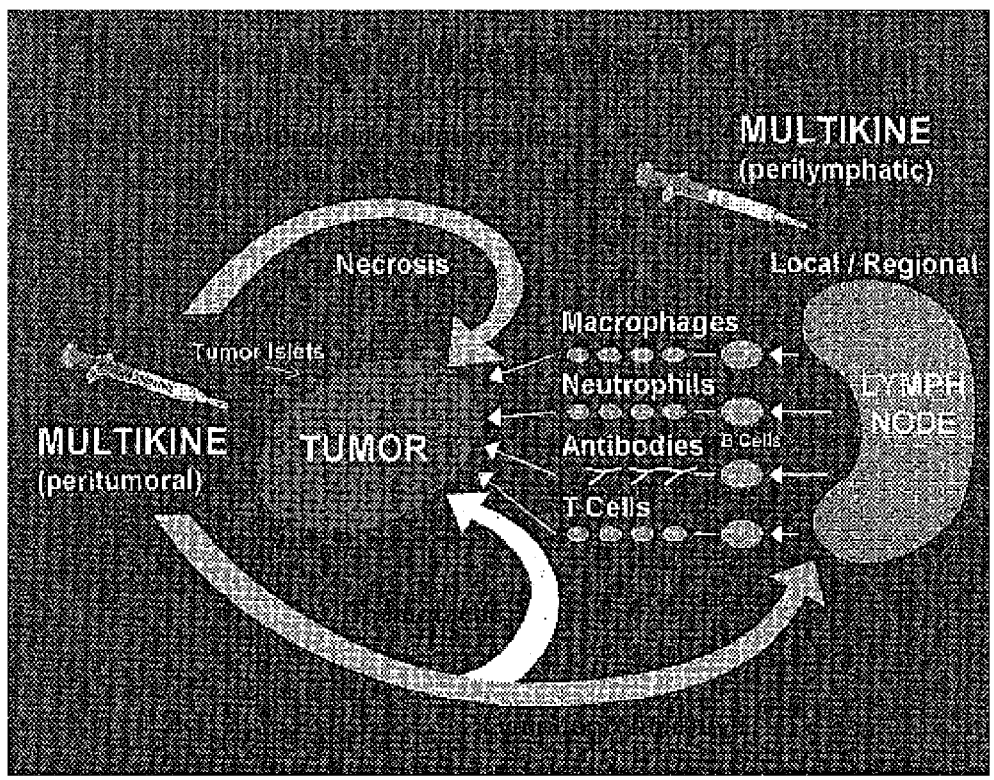
FIG. 1 represents the mode of action of Multikine®.

The present invention is concerned with methods of pre-sensitizing cancer in general and a novel serum-free and mitogen-free cytokine mixture comprised of specific ratios of IL-1β to IL-2, TNF-α to IL-2, IFN-γ to IL-2 and GM-CSF to IL-2. One such novel cytokine mixture is Multikine®, which has demonstrated immuno-modulatory capabilities. The clinical significance of the immuno-suppression in cancer patients unexpectedly impacts methods of pre-sensitizing cancer prior to therapeutic treatment and in particular entry of the tumor cell into a cell cycle phase.

Immune restoration of head and neck cancer patients is accomplished by the infusion of cytokines such as IL-2, IFN α-γ or IL-12. Whiteside, "Immunobiology and immunotherapy of head and neck cancer", *Curr Oncol Rep* 2001;3:46–55. In head and neck cancer, interleukin-based cytokine therapy resulted in immuno-augmenting. Cortesina G et al., "Interleukin-2 injected around tumor-draining lymph nodes in head and neck cancer", *Head Neck* 1991; 13:125–31; De Stefani et al., "Treatment of oral cavity and oropharynx squamous cell carcinoma with perilymphatic interleukin-2: clinical and pathologic correlations", *J Immu-* nother 1996;19:125–33; Valente et al., "Infiltrating leukocyte populations and T-lymphocyte subsets in head and neck squamous cell carcinomas from patients receiving perilymphatic injections of recombinant interleukin 2", Mod Pathol 1990;3:702–8; Whiteside T L et al., "Evidence for local and systemic activation of immune cells by peritumoral injections of interleukin 2 in patients with advanced squamous cell carcinoma of the head and neck", Cancer Res 1990;53:5654–62; Barrera et al., "Combination immunotherapy of squamous cell carcinoma of the head and neck", Arch Otolaryngol Head Neck Surg 2000;126:345–51; Verastegui et al., "A natural cytokine mixture (IRX-2) and interference with immune suppression induce immune mobilization and regression of head and neck cancer", Int J Immunopharmacol 1997;19:619–27; Hadden et al., "Interleukins and contrasuppression induce immune regression of head and neck cancer", Arch Otolaryngol Head Neck Surg 1994;120:395–403. For example, human (r)hIL-2 was successfully used to improve immune function of head and neck cancer patients as measured by cytotoxic T lymphocyte [CTL] and delayed type hypersensitivity [DTH] responses. The decreased response of T cells was shown by the decreased expression of the T cell receptor (TCR), its key signaling components, the $\zeta$ chain and zap-70, the absence of IL-2 production and increased apoptosis of T cells. Whiteside T L., "Immunobiology and immunotherapy of head and neck cancer", Curr Oncol Rep 2001;3:46–55. Studies investigating the causes of the impaired T cell function in head and neck cancer showed that the Fas-FasL system, TGF-$\beta$ and PGE$_2$ are expressed at high levels.

However, in vivo administration of rIL-2 increased density of CD25$^+$ cells as well as natural killer (NK) cells, human leukocyte antigen (HLA)-DR$^+$ lymphocytes and T cells. In another series of studies, positive clinical responses have been observed when a cytokine mixture was administered perilymphatically or peritumorally. However, none of these studies correlated an increased immune response with definitive follow-on treatment such as surgery, radiation therapy and/or chemotherapy.

The Technology

Multikine®, a Leukocyte-Interleukin Injection, is a serum-free, mitogen-free, antibiotic-free preparation produced from human peripheral blood mononuclear cells that include T-cells, B cells and macrophages. There are three "families" of cytokines in Multikine® that together impart the unique biological activity of Multikine®. They include direct cytotoxic/cytostatic and virocidal/virostatic cytokines such as TNF-$\alpha$, and IFN-$\gamma$, lympho-proliferative cytokines such as IL-1, and IL-2 and chemotactic cytokines such as IL-6, IL-8 and MIP-1$\alpha$. Furthermore, the different cytokine and small biological molecules that constitute Multikine® are all derived from the lectin (PHA) in vitro stimulation of human peripheral blood mononuclear cells that include T cells, B cells, and macrophages. Centrifugation on a Ficoll-Paque gradient separates the white blood cells (including T cells, B cells, and macrophages) from donor whole blood, and a series of washes (in physiologically buffered media) facilitates the isolation of lymphocytes, and the removal of red blood cells, cellular debris and other unwanted cellular components from the isolated white cell component of the whole donor blood.

Multikine® contains different cytokines present at specific ratios of each cytokine to Interleukin 2 (IL-2) as follows: IL-1$\beta$ to IL-2 at a ratio range of 0.4–1.5, and preferably at 0.7+/−0.1 (IL-1$\beta$/IL-2), TNF-$\alpha$ to IL-2 at a ratio range of 3.2–10.9, and preferably at 9.5+/−1.8 (TNF-$\alpha$/IL-2), IFN-$\gamma$ to IL-2 at a ratio range of 1.5–10.9, and preferably at 6.0+/−1.1 (IFN-$\gamma$/IL-2), and GM-CSF to IL-2 at a ratio range of 2.2–4.8, and preferably at 4.0+/−0.5 (GM-CSF/IL-2).

The remainder of the different cytokines and other small biologically active molecules in Multikine® are also present within each preparation of the small biologically active molecule to Il-2 as follows: IL-3 to Il-2 in a ratio range of 0.38–0.68, preferably at 0.53+/−0.15, IL-6 to Il-2 in a ratio range of 37.2–53.8, preferably at 46+/−5.9, IL-8 to Il-2 in a ratio range of 261–561.5, preferably at 41+/−10.6, IL-1$\alpha$ to Il-2 in a ratio range of 0.56–0.94, preferably at 0.75+/−0.19, IL-1$\beta$ to Il-2 in a ratio range of 2.87–3.22, preferably at 3.0+/−0.18, IL-16 to Il-2 in a ratio range of 1.24–2.84, preferably at 1.84+/−0.68, G-CSF to Il-2 in a ratio range of 2.16–3.78, preferably at 2.97+/−0.81, TNF-$\beta$ to Il-2 in a ratio range of 1.18–2.43, preferably at 1.8+/−0.63, MIP-1$\alpha$ to Il-2 in a ratio range of 16.78–37.16, preferably at 22.7+/−7.0, MIP-1$\beta$ to Il-2 in a ratio range of 19.2–26.4, preferably at 22.8+/−5.7, a RANTES to Il-2 in a ratio range of 2.3–2.7, preferably at 2.5+/−0.13, a EGF to Il-2 in a ratio range of 0.27–0.28, preferably at 0.275+/−0.008, PGE$_2$ to Il-2 in a ratio range of 3.68–5.42, preferably at 4.5+/−0.87 and TxB$_2$ to Il-2 in a ratio range of 23.5–25.1, preferably at 24.3+/−0.83.

Multikine® was tested using a characterization protocol and does not contain the following cytokines and other small biologically active molecules: IL-4, IL-7, and IL-15, TfR, sICAM, PDGF-AB, IFN-$\alpha$, EPO, LTC 4, TGF-$\beta$2, FGF basic, Angiogenin, sE-selectin, SCF, and LIF. Multikine® contains only trace quantities (just above the level of detection of the assay) of IL-12, and LTB 4.

In the manufacturing process, mononuclear cells are separated from human donor "buffy coats" by step-gradient centrifugation and cultured with PHA to enhance production and secretion of IL-2 and other cytokines from the donor white blood cells in culture as disclosed in U.S. Pat. Nos. 5,093,479, 4,390,623, 4,388,309, 4,406,830, 4,661,447, 4,681,844 and 4,464,355, all of which are incorporated herein by reference. Subsequently, the culture supernatant is aseptically harvested, clarified and subjected to a commercial virus exclusion process. The supernatant is then further concentrated approximately 10 fold by ultrafiltration and microfiltration.

At this point, Human Serum Albumin, Inj. USP is added and the concentrate is then buffered to a physiological pH and brought to a target IL-2 concentration per the label claim (example 400 IU/mL). The concentrate is then subjected to a second micro-filtration (0.22 micron-rated filter) and aseptically dispensed into sterile serum-type vials and labeled by its IL-2 content. Product potency is measured by the incorporation of radio-labeled thymidine by a cytotoxic T-lymphoid line (CTLL-2). The final injectable agent is further tested by ELISA for the presence of five marker cytokines: IL-2, IL-1$\beta$, GM-CSF, IFN-$\gamma$, and TNF-$\alpha$.

Multikine® is provided frozen in a borosilicate glass serum vial containing 2.2 mL of drug at the label claim as IL-2 (400 IU/ml) for peritumoral, intratumoral, perilymphatic or subcutaneous administration. Multikine® is subjected to quality control tests for identity, sterility, bacterial endotoxins, pH, and total protein concentration. Each vial is inspected for particulate contamination and appearance. The preparation has a total protein content of 3 mg/mL wherein the material is supplied sterile and pyrogen free. Multikine® has an assigned expiration date of 24 months from date of manufacture when the drug is stored at −20° C.

Definitions

IL-2—Interleukin 2 (IL-2): A 15.5-kD glycoprotein synthesized by CD4+ helper T lymphocytes (Formally known as T cell Growth Factor). IL-2 has an autocrine effect acting on the CD4+ T lymphocytes that produce it and on other cells of the immune system (including B lymphocytes, CD8+ T lymphocytes, NK [Natural Killer] cells and others).

IL-1β—Interleukin 1 beta (IL-1β): A 17-kD cytokine synthesized by activated mononuclear phagocytes, is found in free form in the circulation and mediates inflammatory responses. It acts on CD4+ T lymphocytes to help facilitate their proliferation, and acts on B-lymphocytes as a growth and differentiation factor. It also induces the synthesis of IL-6 by mononuclear phagocytes.

TNF-α—Tumor Necrosis Factor alpha (TNF-α): A 157 amino acid (aa) residues protein, synthesized by stimulated monocytes, macrophages, B lymphocytes, T lymphocytes, an NK cells among others, found in a trimmeric form in the circulation. TNF mediates direct anti-tumor action, causing tumor cell lysis, facilitates leukocyte recruitment, inducing angiogenesis and promotes fibroblast proliferation.

IFN-γ—Interferon Gamma (IFN-γ): A 21–24-kD glycoprotein homodimer synthesized by activated T lymphocytes and NK cells, is a powerful activator of monocytes increasing monocytes ability to destroy intracellular microorganisms and tumor cells. It has direct anti-viral and anti-proliferative activity, and causes many cell types to express Class II MHC (Major Histocompatibility Complex) cell surface molecular complex, as well as increasing the expression of Class I MHC.

GM-CSF—Granulocyte Macrophage-Colony Stimulating Factor (GM-CSF): A 127 aa protein found as a monomer in the circulation, produced by macrophages and T lymphocytes, fibroblast and endothelial cells. It is a growth factor for hemopoietic cells, and stimulates the growth and differentiation of myelomonocytic lineage.

IL-3—Interleukin—3 (IL-3): A 20-kD Lymphokine synthesized by activated CD4+ T helper lymphocytes, acts as a colony-stimulating factor by facilitating the proliferation of some hematopoietic cells and promoting the proliferation and differentiation of T lymphocytes.

IL-6—Interleukin—6 (IL-6): A 26-kD cytokine produced by activated T lymphocytes, mononuclear phagocytes, endothelial cells, and fibroblasts. It acts on many cells but has a special function in enabling activated B-lymphocytes to differentiate into antibody secreting plasma cells, and induces hepatocytes to form acute-phase proteins (implicated in inflammatory responses) as well as fibrinogen.

IL-8—Interleukin—8 (IL-8): An 8-kD protein produced by macrophages and endothelial cells. Is a powerful chemotactic factor for neutrophils and T lymphocytes, and facilitates neutrophil adherence to endothelial cells.

IL-1α—Interleukin 1 alpha (IL-1α): A 17-kD cytokine (like IL-1β) is cleaved from a 33-kD precursor molecule, synthesized by activated mononuclear phagocytes, is rarely found in free form in the circulation and acts as a membrane-associated substance. It assists IL-1β in mediating inflammatory responses.

IL-10—Interleukin—10 (IL-10): An 18-kD polypeptide produced by CD4+ and CD 8+ T lymphocytes, monocytes, macrophages, activated B lymphocytes, and keratinocytes. It inhibits macrophages ability to present antigen particularly to $T_H1$-type cells, and secrete IL-6 and TNF.

IL-16—Interleukin—16 (IL-16): A 14-kD tetrameric protein produced by CD8+ T lymphocytes, eosinophils, mast cells and respiratory epithelial cells. It has strong chemoattraction properties for CD4+ T lymphocytes and monocytes.

G-CSF—Granulocyte Colony Stimulating Factor (G-CSF): A 22–25-kD homodimer glycoprotein produced by macrophages, endothelial cells, fibroblasts and stromal cells. It increases granulocyte progenitor cells in the marrow, and sustains increase in blood neutrophils. It also enhances the ability of neutrophils to exhibit enhanced super-oxide production thought to be important in the destruction of microbially infected cells and tumor cells.

TNF-β—Tumor Necrosis Factor beta (TNF-β): A 25-kD protein produced by activated lymphocytes. It can kill tumor cells in culture, and stimulates proliferation of fibroblasts. In addition it mimics most of the other actions of TNF-α.

MIP-1α—Macrophage Inflamatory Protein—1 alpha (MIP-1α): A 66-aa monomeric protein produced by macrophages and other cells. It is a chemo-attractant for monocytes, T lymphocytes and eosinophils.

RANTES—An 8-kD protein produced by T lymphocytes and is a chemo-attractant to monocytes, T lymphocytes and eosinophils, and promotes inflammation.

EGF—Epidermal Growth Factor (EGF): A trisulfated polypeptide of 53-aa residues. EGF is a member of the tyrosin kinase family, and has multiple functions including stimulation of the mitogenic response and assisting in wound healing.

$PGE_2$—Prostaglandin $E_2$ ($PGE_2$): $PGE_2$ belong to a family of biologically active lipids derived from arachidonic acid through the cyclooxygenase enzymatic reaction. It is released by activated monocytes and blocks MHC Class II expression on T lymphocytes and macrophages.

$TxB_2$—Thromboxane $B_2$ ($TxB_2$): $TxB_2$ is a member of biologically active compounds derived from polyunsaturated fatty acids by isomerization of prostaglandin and endoperoxidase $PGH_2$ via the enzyme thromboxane synthetase. $TxB_2$ has a physiological role in thromboembolic disease, and anaphylactic reactions.

$CD25^+$ Cells—CD25 is a single chain glycoprotein, often referred to as the α-chain of the Interleukin-2-receptor (IL-2R) or the Tac-antigen, that has a mol wt of 55 kDa and is present on activated T and B cells and activated macrophages. It functions as a receptor for IL2. Together with the β-chain of the IL-2R, the CD25 antigen forms a high-affinity receptor complex for IL-2.

CTLL-2 (Cell Line)—A line of mouse cytotoxic T lymphocytes obtained from C57Bl/6 mice. This T cell line is dependent on an exogenous source of IL-2 for growth and proliferation.

Fas—FasL-The Fas/Fas Ligand system. The combination of a Fas antigen, a cell surface transmembrane protein that mediates apoptosis, and a complementary Fas-activated cytokine on a neutrophil that transduces an apoptotic signal into cells. Fas is a type-I membrane protein belonging to the tumor necrosis factor (TNF) receptor superfamily, and FasL is a member of the TNF family. FAS ligand is a membrane-bound protein of 31 kDa [kilo Dalton] (278 amino acids). The Fas-Fas ligand system plays important roles in many biological processes, including the elimination of autoreactive lymphoid cells. The Fas ligand is predominantly expressed in activated T lymphocytes and is one of the major effector molecules of cytotoxic T lymphocytes and natural killer cells.

$HLA-DR^+$ Lymphocytes—Lymphocytes containing human leukocyte antigen (HLA)-DR antigens, a group of polymorphic glycoproteins determined by a glue sequence. found in a leukocyte loci located on chromosome 6, the major histocompatibility loci in humans.

IU (International Units)—A unit of measure of the potency of biological preparations by comparison to an international reference standard of a specific weight and strength e.g., WHO $1^{st}$ International Standard for Human IL-2, 86/504. International Units are the only recognized and standardized method to report biological activity units that are published and are derived from an international collaborative research effort.

U (Units as a measure of biological activity)—Shorthand for a variety of named "units", which each laboratory derives as a reference, which is further unique to the laboratory where the work is being performed. Each "unit" is different from one laboratory to another laboratory and is not a globally recognized standard such as International Units (IU).

Mononuclear Infiltrate—Presence of monocytes, plasma cells, and lymphocytes, in tissue where they "normally" would not be present; or the presence of these cells in large numbers or abundance in clusters where they would otherwise be present in only a small number.

TCR ζ Chain—T-cell receptor-zeta chain. The zeta subunit is part of the TCR complex and is targeted towards the interaction of the TCR cell surface receptor with its ligand (antigen). The zeta subunit extending into the cell cytoplasm (cytosol) is phosphorylated at its tyrosine residues upon T cell activation and is implicated in signal transduction after TCR ligation.

TIL (Tumor Infiltrating Lymphocytes)—T lymphocytes isolated from the tumor they are infiltrating. Tumor Infiltrating lymphocytes have little or no cytotoxicity. TILs include CD4+ CD8+ predominantly T cells, and can be expanded in vitro by culture in the presence of IL-2. These cells are activated by the treatment with IL-2 and are frequently more aggressive towards the tumor from which they were isolated than normal lymphokine activated cells. The cytotoxic activity of TILs can be enhanced by IFN-γ. The antitumor activity of TILs in vivo can be blocked by TGF-β.

ZAP 70—A 70 kD Zeta Associated Protein associated with the TCR ζ Chain that is a tyrosine kinase present in cytosol. ZAP 70 is thought to participate in maintaining T lymphocyte receptor signaling, mediating the signal transduction which eventually produces IL-2. The ZAP70 gene is expressed in T-cells and natural killer cells and maps to human chromosome 2q12.

ζ (Zeta) Chain—See TCR ζ Chain—The zeta chain gene is located on chromosome 1 in humans. The extracellular domain of this protein is nine amino acids long whereas the transmembrane domain contains a negatively charged aspartic acid residue and the cytoplasmic domain is 113 amino acids long. The cytoplasmic tail contains three of the antigen recognition motifs found in the cytoplasmic tails of CD3 chains. The zeta chain is also associated with other receptors such as the Fc (fragment, crystalline)-gamma receptor of NK cells.

USP—U.S. Pharmacopeia Monographs.

P—"p<0.01": A term in mathematical statistics that denotes the level of probability of an event occurring under pre-set conditions.

ANOVA (Analysis of Variances)—A single factor analysis as described in Statistics and mathematical textbooks e.g., "Handbook of Statistical Methods for Engineers and Scientists", Harrison M. Wadsworth, Jr., Ed., McGraw Hill 1990, and "Statistical Operations Analysis of Health Research Data", Robert P. Hirsch and Richard K. Riegelman, Eds. Blackwell Science Inc., 1996.

Mode of Action and Characterization of Multikine®

Multikine® is a biologically active, minimally toxic, immunomodulatory mixture of naturally derived and naturally occurring human cytokines produced under set conditions as described herein. Multikine® can be used as a anti-cancer and anti-viral therapy or as a neo-adjuvant therapy with a broad-spectrum application for cancer, infectious disease, and other diseases states responding to immunomodulation.

Multikine® was developed based on animal studies, which demonstrated that "mixed interleukins" have immunomodulatory and immunostimulatory activity in vitro as shown by Hadden et al., "Mixed Interleukins and Thymosin Fraction V Synergistically Induce T Lymphocyte Development in Hydrocortisone-Treated Aged Mice", *Cell. Immunol.* 144:228–236 (1992). Without being limited to any one theory, it is hypothesized that the local/regional injection of "mixed interleukins" such as Multikine® overcomes local immuno-suppression. Subsequently, a break tolerance to tumor antigens occurs and allows for an effective local anti-tumor immune response to occur.

It has been shown that the local instillation of interleukins in the region of the tumor or the actual transfection of Interleukin genes into a tumor markedly augments the anti-tumor immune response resulting in tumor regression as reported by Golumbek et al., "Treatment of Established Renal Cancer by Tumor Cells Engineered to Secrete Interleukin-4", *Science* 254:713–716 (1991). However, none of these studies discovered the highly unexpected effect of inducing malignant cells into a cell cycle phase without causing the active proliferation of the tumor.

Quite unexpectedly, the administration of Multikine® pre-surgery leads to an increase in the number of tumor cells in the cell cycle phase without increasing the risk of a more rapidly growing and more rapidly recurring tumor as would otherwise be predicted from the art. The ability to induce tumor cells into cell-cycle appears to be unique to Multikine® and may be due to the synergistic effect of the different cytokines present in this investigational drug and the differential effect of these cytokines on both the host's immune system and the tumor cells.

Data regarding the recurrence rate of patients treated with Multikine® prior to surgery showed no recurrence of cancer at 24 months post treatment with Multikine®. Remarkably, a small cohort of 8 sequentially treated patients did not have a single recurring patient in the 24 months follow-up period. In stark contrast, the literature teaches the recurrence rate of similar patients at about 50% at 18–24 months post surgery.

In particular, Multikine® treatment did not appear to induce active proliferation of tumor residing lymphoid cells. Correspondingly, stromal Ki-67$^+$ cells decreased while the frequency of Ki-67$^+$ cancer cells increased following Multikine® treatment. Thus, Multikine® treatment induced an increase in the number of cycling tumor cells leading to increased susceptibility of the residual tumor to follow-on treatment with radiation and/or chemotherapy. Although other studies conducted with both natural and recombinant cytokines have shown efficacy in the treatment of cancer therapy, those studies have failed to teach the induction of entry into the cell cycling phase or the new method of synergistically combining Multikine® with chemotherapy, immuno-therapy and radiation therapy.

For example, studies with the use of natural human and recombinant IL-2 and other cytokines as well as in local-regional therapy demonstrated the immune augmenting and anti-cancer activity at various sites. In particular, IL-2 demonstrates activity in the pleural cavity, liver and the urinary bladder while IFN-α demonstrates activity in the ovary while IFN-β demonstrates activity in the brain as reported by Yasumoto et al., "Induction of lymphokine-activated killer cells by intrapleural instillations of recombinant interleukin-2 in patients with, malignant pleurisy due to lung cancer", *Cancer Res* 1987;47:2184–7; Mavilgit et al., "Splenic versus hepatic artery infusion of interleukin-2 in patients with liver metastases", *J Clin Oncol* 1990;8:319–24; Pizza et al., "Tumor regression after intralesional injection of interleukin-2 (IL-2) in bladder cancer. Preliminary report", *Int J Cancer* 1984;34:359–67; Berek et al., "Intraperitoneal recombinant α-interferon for "salvage" immunotherapy in stage III epithelial ovarian cancer: a gynecologic oncology group study", *Cancer Res* 1985;45:4447–53; and Fettel et al., "Intratumor administration of beta-interferon in recurrent malignant gliomas-A phase I clinical and laboratory study", *Cancer* 1990;65:78–83. Even further, IFN-γ has been shown to demonstrate activity in skin while TNF-α demonstrates activity in the genitalia while a mixture of various cytokines demonstrates activity in the head and neck as reported by Edwards et al., "The effect of intralesional interferon gamma on basal cell carcinomas", *J Am Acad Dermatol* 1990;22:496–500; Irie et al., "A case of vulva cancer responding to the recombinant human tumor necrosis factor (PT-950) local injection therapy", *Gan No Rinsho* 1988;34:946–50; and Pulley et al., "Intravenous, intralesional and endolymphatic administration of lymphokines in human cancer", *Lymph Res* 1986;5:S157–63. Moreover, studies of recombinant IL-2 administrations for 10 days prior to surgery in the jugular peri-lymphatic or jugular peri-lymphatic and under the chin showed variable necrosis and lymphocytic infiltration as reported by Valente et al., "Infiltration leukocyte polulations and T-lymphocyte subsets in head and neck squamous cell carcinomas from patients receiving perilymphatic injections of recombinant interleukin-2", *Mod Pathol* 1990;3:702–8 and DeStefani et al., "Treatment of oral cavity and oropharynx squamous cell carcinoma with perilymphatic interleukin-2: clinical and pathologic correlations", *J Immunother* 1996;19:125–33. Moreover, microscopic examination of the resected tumors demonstrated an increase in lymphocytic infiltrate correlating to the clinical observations of IL-2 as reported by Saito et al., "Immunohistology of tumor tissue in local administration of recombinant interleukin-2 in head and neck cancer", *Nip Jibi Gakkai Kaiho* 1989;92:1271–6.

Nevertheless, none of the aforementioned studies showed any change in the gross dimensions of resected tumors despite two remissions at putatively high doses of recombinant IL-2 (800,000 U for four weeks [U=Units]) in 20 head and neck cancer patients as reported by Saito et al., "Clinical evaluation of local administration of rIL-2 in head and neck cancer", *Nip Jibi Gakkai Kaiho.* 1989;921271–6. Furthermore, the aforementioned studies have been limited by the small number of patients and hampered by the lack of a pathological comparison to a control group.

Although a recent randomized multi-center phase III study of 202 OSCC patients by De Stefani et al. indicated that peri-lymphatic administration of low does (5000 U/day [U=Units]) of recombinant human IL-2 for 10 days prior to surgery, into the ipsylateral cervical lymph node chain, resulted in a significant ($p<0.01$) increase in disease-free survival, which in turn resulted in longer overall survival ($p<0.03$), De Stefani et al. failed to assess the role of this treatment regimen on cell cycling and its effect on the improvement of radiation and chemotherapy. See De Stefani et al., "Improved Survival With Perilymphatic Interleukin 2 in Patients With Resectable Squamous Cell Carcinoma of the Oral Cavity and Oropharynx", *Cancer* 2002; 95:90–97. Furthermore, despite teaching 5000 U/day, no comparisons between the present invention and De Stefani et al. could be made with regard to De Stefani et al.'s teaching of a "high" and "low" dose of an administered biologic because the drug potency was measured by an undefinable U (Units). In contrast, the present invention validated and completed the full USP analytical methods validation program for determining the biological activity of Multikine® in IU (International Units).

Methods

Tumor cell proliferation as measured by the immunohistochemistry Ki-67 marker, or other equivalent means such as through the use of PCNA marker, p53 marker were used as a prognostic parameter. de Vicente et al., "Expression of cyclin D1 and Ki-67 in squamous cell carcinoma of the oral cavity: clinicopathological and prognostic significance", *Oral Oncol* 2002; 38:301–8; Bettendorf et al., "Prognostic relevance of Ki-67 antigen expression in 329 casess of oral squamous cell carcinoma", *ORL J Otorhinolaryngeol Relat Spec* 2002;64:200–5. In conjunction, flow cytometry or conventional staining methods and the use of microscopy with clinical, histopathological and tumor staging and classification (TNM, Tumor, Node, Metastasis) were used with other to indicate the aggressiveness of the disease process. Kerdpon et al., "Expression of p53 in oral mucosal hyperplasia, dysplasia and squamous cell carcinoma", *Oral Disease* 1997;3:86–92.

In particular, a Ki67 cell proliferation marker differentiates and is specific for only the cells that are in the cell cycle stages. $G_1$ is the first growth phase; S is the second phase marked by the initiation of DNA synthesis by the cell where cellular DNA replicates, and $G_2$ the second growth phase of the cell follows DNA replication in which the cell doubles in size. M is the last phase in the cell cycle where mitosis occurs wherein the cell divides into a daughter cell from the original parent cell. Each resulting cell contains a complete replica of the DNA of the original parent cell. Ki67 cellular marker being specific to cells in the cell cycle cannot be found in cells that are in $G_0$, which is a resting phase of the cell. During $G_0$, the cell does not undergo cellular replication, proliferation or DNA replication. Notably, the cell cycle phase phenomena is a property common to all living eukaryotic cells including tumor cells.

To detect tumor cell proliferation, the presence of Ki-67 in residual tumor cell nests following surgical excision are determined. Raybaud et al., "Nuclear DNA content, an adjunct to p53 and Ki-67 as a marker of resistance to radiation therapy in oral cavity and pharyngeal squamous cell carcinoma", *Int J Oral Maxillofac Surg* 2000; 29:36–41; Koelbl et al., "p53 and Ki-67 as predictive markers for radiosensitiveity in squamous cell carcinoma of the oral cavity? An immunohistochemical and clinicopathologic study", *Int J Radiat Oncol Biol Phys* 2001;49:147–54. Generally, Ki-67 can be found in cells undergoing cell cycle $G_1$, S, $G_2$, and M but not in "resting" tumor cells ($G_0$). Since cycling tumor cells are both more radio- and chemo-sensitive, and non-cycling tumor cells are by-and-large radio- and chemo-resistant.

Accordingly, a study was designed that would analyze by immuno-histopathology tumors from head and neck cancer patients treated with Multikine® prior to surgical resection of the residual tumor followed by radiation therapy. Timar et al., "The effect of Leukocyte Interleukin, Injection on the peri- and intratumoral subpopulation of mononuclear cells and on tumor epithelia—A possible new approach to augmenting sensitivity to radiation and chemotherapy in oral cancer. A multi-center Phase I/II clinical trial", *The Laryngoscope* [accepted for publication June 2003]. The study was conducted in a blinded manner and executed by three independent qualified pathologists that were blinded to the treatment and patient population, treated or control. Our clinical study, the results of which are reported here, and are incorporated herein by reference analyzed a cohort of 54 oral squamous cell cancer patients (H&NC) as part of a phase I–II clinical trial. These patients were investigated for safety of the therapeutic regimen, tumor and clinical responses, and for the composition of the mononuclear infiltrate and cell cycling rates.

Twenty-seven (27) patients of the 54 patients cohort received peritumoral administration of Multikine® in a dose escalating study. This study resulted in the demonstration that the pre-treatment of head and neck cancer patients with Multikine® tumor induced entry into cell cycle phase, $G_1$, S, $G_2$, and M, but not $G_0$. This lead to a decrease in recurrence rate and an increase in disease-free survival of Multikine® treated patients.

In our study, Multikine® administrations were performed in the following manner: daily dose was injected peritumorally over a two-week period (3 times per week) at the following doses for each of the dose groups tested; low dose, 400 IU (International Units of IL-2) [IL-2-equivalent] daily (8 patients), medium dose, 800 IU (IL-2-equivalent) daily (12 patients), and 5 times per week at the high dose, 800 IU (IL-2-equivalent) daily (7 patients). All Multikine® injections were administered intradermally at the circumferential margin of the visible/palpable tumor mass. Surgery aimed at resection of the residual tumor mass was performed between day 21 and day 28 following the initial administration of Multikine®. Local/regional radiation therapy commenced in post-operative patients following wound healing at variable times post-surgery and was dependent on the individual patient recovery from the surgical intervention. Radiotherapy was generally initiated between two to four weeks post-surgery.

The administration of Multikine® was preceded by the single intravenous infusion of cyclophosphamide, 300 mg/m$^2$ three-days prior to the first Multikine® administration. Indomethacin (25 mg) was self-administered orally (with food), three times daily, beginning 3 days post cyclophosphamide administration and until 24 hours prior to surgery. Zinc sulfate (50 mg) and multivitamin supplement, once daily, was self-administered beginning 3 days after cyclophosphamide administration and until 24 hours prior to surgery. The patients were counseled and encouraged to continue self-administration of multivitamin and Zinc regimen following surgery. These agents have no effect whatsoever on tumor cell cycling and were given at doses that are 3–5 fold bellow the normal cancer therapeutic doses for these drugs.

Results

Figure 2:
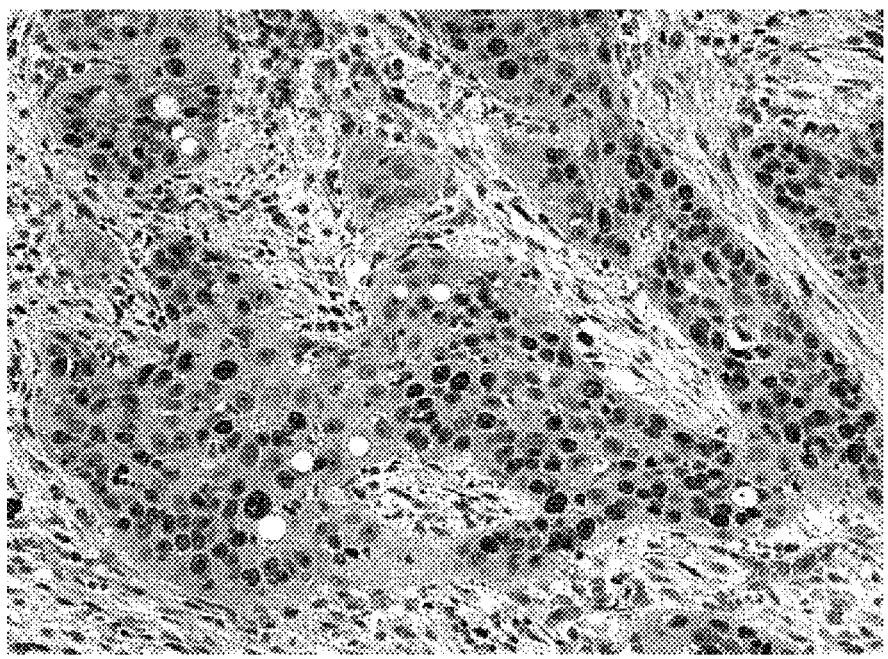
FIG. 2 represents the immuno-histochemistry staining of a tumor in head and neck cancer squamous cell carcinoma with the specific cell cycle marker Ki-67.
Figure 3:
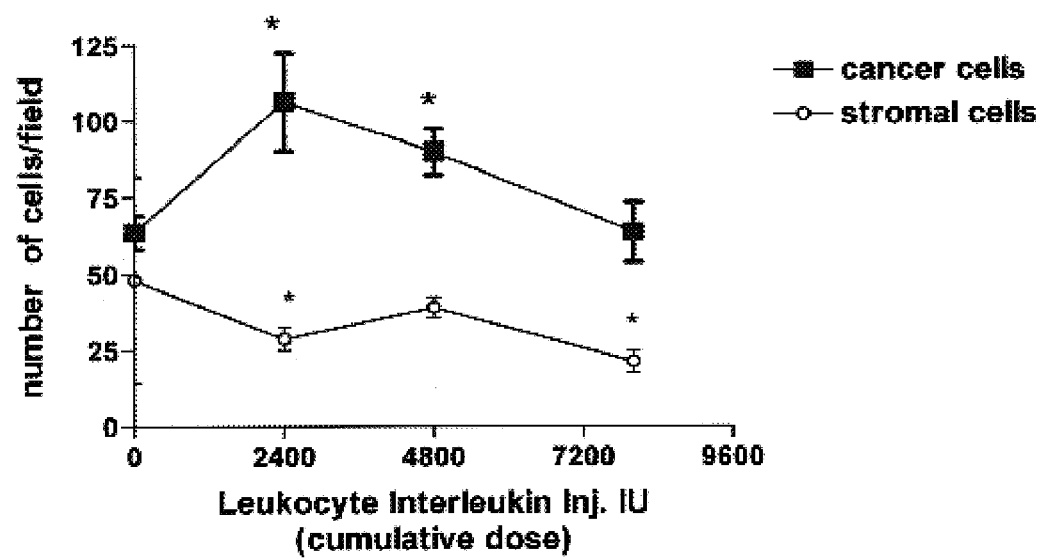
FIG. 3 represents morphometric analysis of Ki-67 immuno-histochemistry staining of both tumor stroma and tumor epithelia where "*" marks a statistically significant difference where $p<0.05$ [at α=0.05].

Detection of cycling cells by Ki-67 expression identified cancer cells as shown in FIG. 1 and stromal cells (host cells: mononuclear cells, fibroblasts, endothelial cells etc.). Morphometric analysis of the density of Ki-67$^+$ cancer cells indicated that Multikine® treatment induced significant increase ($p<0.05$) in cycling tumor cells except at the highest Multikine® dose administered as shown in FIG. 2. On the other hand, the incidence of cycling host cells found primarily in the stromal area of the tumor decreased with an increasing Multikine® dose again shown in FIG. 2. Effects were proved to be significant for the lowest and the highest doses ($p<0.05$). These findings support the conclusion that treatment with Multikine® treatment causes cancer cells to enter a cell cycle phase but does not cause the host immune cells or stromal cells to cycle.

Accordingly, the present invention contemplates Multikine® treatment to induce cell cycle entry of a high proportion of the tumor cell population based on the expression of Ki-67 antigen.

As stated herein, preliminary data regarding the recurrence rate of patients treated with Multikine® prior to surgery, which were either followed by radiation therapy or watchful waiting, did not exhibit an increase in the recurrence rate at 24 months post treatment with Multikine®. A small cohort of 8 sequentially Multikine® treated patients did not have a single recurring patient in the 24 months follow-up period. In contrast, the literature pegs the recurrence rate of these patients at about 50% at 18–24 months post surgery.

Moreover, Multikine® treatment did not appear to induce active proliferation of tumor residing lymphoid cells, and correspondingly stromal Ki-67$^+$ cells decreased, while the frequency of Ki-67$^+$ cancer cells increased following Multikine® treatment. Thus, Multikine® treatment induced the increase the number of cycling tumor cells leading to increased susceptibility of the residual tumor to follow-on treatment with radiation and/or chemotherapy.

Treatment Regimen with Multikine® for Cancer

The treatment regimen for the pre-sensitization of cancer with Multikine® is predicated on treatment protocol developed for head and neck cancer patients, which has been proven in a statistically significant manner to significantly increase tumor cell cycling aimed at rendering these tumor cells more sensitive to follow on treatment with radiation and/or chemotherapy.

The treatment will include the administration of Multikine® subcutaneously in the area of the submandibular cervical lymph node chain.

A two-week course of ten (10) subcutaneous/subdermal daily injections of Multikine® at a daily dose ranging from about 20 IU to 1600 IU as IL-2 and will be administered ½ peritumorally at the circumferential margin of the tumor mass, and ½ at the submandibular lymphatic chain ipsylateral to the tumor mass. Another course of treatment can preferably be in the range of 40 IU to 800 IU. Still another range can be in the range of 35 IU to 75 IU.

One specific non-limiting example of a suggested treatment contemplates administration of Multikine® at a daily dose of 55 IU as IL-2 in a two-week course of ten (10) subcutaneous/subdermal daily injections Drug Safety, Pilot Efficacy and Compositions Multikine® has been tested in over 190 Cancer, HIV, and HIV/HPV infected, patients with no severe adverse events related to Multikine® administration as reported by Harris et al., "Immunologic approaches to the treatment of prostate cancer", *Semin Oncol.* 1999 August;26(4):439–7; Timar et al., "The effect of Leukocyte Interleukin, Injection on the peri-and intratumoral subpopulation of mononuclear cells and on tumor epithelia—A possible new approach to augmenting sensitivity to radiation and chemotherapy in oral cancer. A multi-center Phase I/II clinical trial", *The Laryngoscope* [accepted for publication June 2003]; Brown et al., "A Phase I Open-Label Study of Leukocyte Interleukin, Injection in HIV-1 infected individuals: preliminary evidence for improved delayed-type hypersensitivity responses to recall antigens", *Antiviral Therapy* 5 (supplement) 18, 2000; Taylor et al., "Immunotherapy with Leukocyte Interleukin, Injection for human papilloma virus (HPV) induced cervical dysplasia in HIV patients", Annual Meeting of the International Society for Interferon and Cytokine Research, Cleveland, Ohio, October 2001; Taylor et al., "Immunotherapy with Leukocyte Interleukin, Injection for human papilloma virus (HPV) induced cervical dysplasia in HIV patients", 33rd SGO Conference, Miami, Fla., March 2002 Multikine® was also shown to be safe in animal toxicological studies in mice, rats, guinea pigs and dogs.

Furthermore, Multikine® was tested for and has demonstrated pilot efficacy in head and neck cancer and cervical dysplasia.

Multikine® may further be used as a component of an immunomodulatory composition together with one or more pharmaceutically acceptable carriers or adjuvants, either prophylactically or therapeutically. When provided for use prophylactically, the immunomodulatory composition is provided in advance of any evidence of infection or disease. While it is possible for Multikine® to be administered in a pure or substantially pure form, a pharmaceutical composition, formulation or preparation may also be used.

The formulations of the present invention, both for clinical and for human use, comprise Multikine® as described above together with one or more pharmaceutically acceptable carriers and, optionally, other therapeutic ingredients, especially therapeutic immunological adjuvants. The carrier (s) must be "acceptable" in the sense of being compatible with the other ingredients of the formulation and not deleterious to the recipient thereof.

In general, the formulations are prepared by uniformly and intimately bringing into association the active ingredient with liquid carriers or finely divided solid carriers or both, and then, if necessary, bringing the product into the desired formulation. The term "pharmaceutically acceptable carrier" as used herein refers to any carrier, diluent, excipient, suspending agent, lubricating agent, adjuvant, vehicle, delivery system, emulsifier, disintegrant, absorbant, preservative, surfactant, colorant, flavorant, or sweetener. The formulations may conveniently be presented in unit dosage form and may be prepared by any method well-known in the pharmaceutical art.

Formulations suitable for intravenous, intranuscular, subcutaneous, or intraperitoneal, nasal, etc. administration conveniently comprise sterile aqueous solutions of the active ingredient(s) with solutions which are preferably isotonic with the blood of the recipient. The compounds of the present invention may also be administered orally, parenterally, by inhalation spray, topically, rectally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrastemal and intracranial injection or infusion techniques.

Such formulations may be conveniently prepared by dissolving solid active ingredients in water containing physiologically compatible substances such as sodium chloride (e.g. 0.1–2.0M), glycine, and the like, and having a buffered pH compatible with physiological conditions to produce an aqueous solution and rendering the solution sterile. These may be present in unit or multi-dose containers, for example, sealed ampules or vials.

The compounds of the present invention may also be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil may be employed including synthetic mono- or di-glycerides. Fatty acids such as oleic acid and its glyceride derivatives, including olive oil and castor oil, especially in their polyoxyethylated versions are useful in the preparation of injectables. These oil solutions or suspensions may also contain long-chain alcohol diluents or dispersants.

The compounds of this invention may also be administered topically, especially when the conditions addressed for treatment involve areas or organs readily accessible by topical application including disorders of the eye, the skin, or the lower intestinal tract. Suitable topical formulations are readily prepared for each of these areas.

For topical application to the eye, or ophthalmic use, the compounds can be formulated as micronized suspensions in isotonic, pH adjusted sterile saline, or preferably, as solutions in isotonic, pH adjusted sterile saline, either with or without a preservative such as benzylalkonium chloride. Alternatively, the ophthalmic uses of Multikine® may be formulated in an ointment such as petrolatum.

For topical application to the skin, the compounds can be formulated in a suitable ointment containing the compound suspended or dissolved in, for example, a mixture with one or more of the following: mineral oil, liquid petrolatum, white petrolatum, propylene glycol, polyoxyethylene poly-oxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

The amount of active ingredient that may be combined with the carrier materials to produce a single dosage form will vary depending upon the host treated and the particular mode of administration. Some factors include the activity of the specific compound employed, the age, body weight, general health, sex, and diet of the patients; the time of administration, rate of excretion, drug combination, and the severity of the particular disease being treated and form of administration.

Pharmaceutical methods may also be employed to control the duration of action. Controlled release preparations may be achieved through the use of polymer to complex or absorb the peptide. The controlled delivery may be exercised by selecting appropriate macromolecules (for example, polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release.

For example, Multikine® may be incorporated into a hydrophobic polymer matrix for controlled-release over a period of days. Such controlled-release films are well known to the art. Particularly preferred are transdernal delivery systems. Other examples of polymers commonly employed for this purpose that may be used in the present invention include non-degradable ethylene-vinyl acetate copolymer and degradable lactic acid-glycolic acid copolymers which may be used externally or internally. Certain hydrogels such as poly(hydroxyethylmethacrylate) or poly(vinylalcohol) also may be useful, but for shorter release cycles then the other polymer releases systems, such as those mentioned above.

Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly (methylmethacrylate) microcapsules, respectively, or in colloidal drug delivery systems, for example, liposomes, albumin microspheres, microemulsions, nanoparticles, and nanocapsules or in macroemulsions.

To be effective therapeutically as central nervous system targets, Multikine® should also readily penetrate the blood-brain barrier when peripherally administered. Compounds which cannot penetrate the blood-brain barrier can be effectively administered by an intraventricular route or other appropriate delivery system suitable for administration to the brain.

Multikine® may also be supplied in the form of a kit, alone, or in the form of a pharmaceutical composition as described above. Administration of Multikine® can be conducted by conventional methods. For example, Multikine® can be used in a suitable diluent such as saline or water, or complete or incomplete adjuvants. Multikine® can be administered by any route appropriate for immune system stimulation, such as intravenous, intraperitoneal, intramuscular, subcutaneous, nasal, oral, rectal, vaginal, and the like.

As noted above, Multikine® may be for either a prophylactic or therapeutic purpose. When provided prophylactically, Multikine® is provided in advance of any evidence or in advance of any symptom due to disease. When provided therapeutically, Multikine® is provided at (or after) the onset of the disease or at the onset of any symptom of the disease. The therapeutic administration of Multikine® serves to attenuate the disease and improves conventional treatment outcomes.

The invention being thus described, it will be obvious that the same may be varied in many ways. Such variations are not to be regarded as a departure from the spirit scope of the invention and all such modifications are intended to be included within the scope of the following claims.

I claim:

1. A serum-free and mitogen-free cytokine mixture, comprising specific ratios of cytokines selected from the group of IL-1β, TNF-α, IFN-γ and GM-CSF to Interleukin-2 (IL-2) as follows:

IL-1β to IL-2 at a ratio range of 0.4–1.5;

TNF-α to IL-2 at a ratio range of 3.2–11.3;

IFN-γ to IL-2 at a ratio range of 1.5–10.9; and

GM-CSF to IL-2 at a ratio range of 2.2–4.8 with the proviso that IL-12 is present in only trace quantities.

2. The serum-free and mitogen-free cytokine mixture of claim 1, wherein said specific ratios of cytokines are as follows:

IL-1β to IL-2 at a ratio range of 0.6 to 0.8;

TNF-α to IL-2 at a ratio range of 7.7 to 10.9;

IFN-γ to IL-2 at a ratio range of 4.9 to 7.1; and

GM-CSF to IL-2 at a ratio range of 3.5 to 4.5.

3. A pharmaceutical composition for use in treating cancer, comprising specific ratios of cytokines selected from the group of IL-1β, TNF-α, IFN-γ and GM-CSF to Interleukin-2 (IL-2) as follows:

IL-1β to IL-2 at a ratio range of 0.4–1.5;

TNF-α to IL-2 at a ratio range of 3.2–11.3;

IFN-γ to IL-2 at a ratio range of 1.5–10.9;

GM-CSF to IL-2 at a ratio range of 2.2–4.8, with the proviso that IL-12 is present in only trace quantities and optionally in combination with a pharmaceutically acceptable excipient, carrier or additive.

4. The pharmaceutical composition of claim 3, wherein said specific ratios of cytokines are as follows:

IL-1β to IL-2 at a ratio range of 0.6 to 0.8;

TNF-α to IL-2 at a ratio range of 7.7 to 10.9;

IFN-γ to IL-2 at a ratio range of 4.9 to 7.1; and

GM-CSF to IL-2 at a ratio range of 3.5 to 4.5.

* * * * *

UNITED STATES PATENT AND TRADEMARK OFFICE
CERTIFICATE OF CORRECTION

PATENT NO. : 6,896,879 B2
DATED : May 24, 2005
INVENTOR(S) : Eyal Talor

It is certified that error appears in the above-identified patent and that said Letters Patent is hereby corrected as shown below:

Column 3, line 64 to Column 4, line 19,
Should read as follows:
-- In other specific applications, the serum-free and mitogen-free cytokine preparation or pharmaceutical composition has further different cytokines and other small biologically active molecules in Multikine® wherein the ratio of each of the small biologically active molecules to IL-2 is as follows: IL-3 to IL-2 in a ratio range of 0.38 - 0.68, preferably at 0.53 +/-0.15, IL-6 to IL-2 in a ratio range of 37.2 - 53.8, preferably at 46 +/-5.9, IL-8 to IL-2 in a ratio range of 261 - 561.5, preferably at 411 +/-10.6, IL-1α to IL-2 in a ratio range of 0.56 - 0.94, preferably at 0.75 +/-0.19, IL-10 to IL-2 in a ratio range of 2.82 - 3.22, preferably at 3.0 +/-0.18, IL-16 to IL-2 in a ratio range of 1.16 - 2.84, preferably at 1.84 +/-0.68, G-CSF to IL-2 in a ratio range of 2.16 - 3.78, preferably at 2.97 +/-0.81, TNF-β to IL-2 in a ratio range of 1.17 - 2.43, preferably at 1.8 +/-0.63, MIP-1α to IL-2 in a ratio range of 15.7 - 37.16, preferably at 22.7 +/-7.0, MIP-1β to IL-2 in a ratio range of 17.1 - 28.5, preferably at 22.8 +/-5.7, a RANTES to IL-2 in a ratio range of 2.3 - 2.7, preferably at 2.5 +/-0.13, a EGF to IL-2 in a ratio range of 0.267 - 0.283, preferably at 0.275 +/-0.008, $PGE_2$ to IL-2 in a ratio range of 3.63 - 5.42, preferably at 4.5 +/-0.87 and $TxB_2$ to IL-2 in a ratio range of 23.47 - 25.13, preferably at 24.3 +/-0.83. --.

Column 6,
Lines 4-23 should read as follows:
-- The remainder of the different cytokines and other small biologically active molecules in Multikine® are also present within each preparation of the small biologically active molecules to IL-2 as follows: IL-3 to IL-2 in a ratio range of 0.38 - 0.68, preferably at 0.53 +/-0.15, IL-6 to IL-2 in a ratio range of 37.2 - 53.8, preferably at 46 +/-5.9, IL-8 to IL-2 in a ratio range of 261 - 561.5, preferably at 411 +/-10.6, IL-1α to IL-2 in a ratio range of 0.56 - 0.94, preferably at 0.75 +/-0.19, IL-10 to IL-2 in a ratio range of 2.82 - 3.22, preferably at 3.0 +/-0.18, IL-16 to IL-2 in a ratio range of 1.16 - 2.84, preferably at 1.84 +/-0.68, G-CSF to IL-2 in a ratio range of 2.16 - 3.78, preferably at 2.97 +/-0.81, TNF-β to IL-2 in a ratio range of 1.17 - 2.43, preferably at 1.8 +/-0.63, MIP-1α to IL-2 in a ratio range of 15.7 - 37.16, preferably at 22.7 +/-7.0, MIP-1β to IL-2 in a ratio range of 17.1 - 28.5, preferably at 22.8 +/-5.7, a RANTES to IL-2 in a ratio range of 2.3 - 2.7, preferably at 2.5 +/-0.13, a EGF to IL-2 in a ratio range of 0.267 - 0.283, preferably at 0.275 +/-0.008, $PGE_2$ to IL-2 in a ratio range of 3.63 - 5.42,

UNITED STATES PATENT AND TRADEMARK OFFICE
CERTIFICATE OF CORRECTION

PATENT NO. : 6,896,879 B2
DATED : May 24, 2005
INVENTOR(S) : Eyal Talor

It is certified that error appears in the above-identified patent and that said Letters Patent is hereby corrected as shown below:

Column 6 (cont'd),
preferably at 4.5 +/-0.87 and $TxB_2$ to IL-2 in a ratio range of 23.47 - 25.13, preferably at 24.3 +/-0.83. --.

Signed and Sealed this

Twenty-seventh Day of September, 2005

JON W. DUDAS
*Director of the United States Patent and Trademark Office*